United States Patent
Kijowski et al.

(10) Patent No.: US 9,606,037 B2
(45) Date of Patent: Mar. 28, 2017

(54) FLUID CONTAINER WITH FLUID IDENTIFICATION SENSOR AND METHOD

(71) Applicant: Aesynt Incorporated, Cranberry Township, PA (US)

(72) Inventors: Todd Kijowski, Natrona Heights, PA (US); Paul Santmyer, Harmony, PA (US); Thaddeus Hartlaub, Baden, PA (US); David Deutsch, Evans City, PA (US)

(73) Assignee: Aesynt Incorporated, Warrendale, PA (US)

( * ) Notice: Subject to any disclaimer, the term of this patent is extended or adjusted under 35 U.S.C. 154(b) by 50 days.

(21) Appl. No.: 14/604,230

(22) Filed: Jan. 23, 2015

(65) Prior Publication Data

US 2016/0213565 A1    Jul. 28, 2016

(51) Int. Cl.
| | |
|---|---|
| *G01N 9/36* | (2006.01) |
| *G01N 33/15* | (2006.01) |
| *A61J 1/10* | (2006.01) |
| *A61J 1/14* | (2006.01) |

(52) U.S. Cl.
CPC ............. *G01N 9/36* (2013.01); *G01N 33/15* (2013.01); *A61J 1/10* (2013.01); *A61J 1/1475* (2013.01); *A61J 2200/70* (2013.01)

(58) Field of Classification Search
None
See application file for complete search history.

(56) References Cited

U.S. PATENT DOCUMENTS

| | | | | |
|---|---|---|---|---|
| 3,523,530 A | * | 8/1970 | Pagones | A61M 5/158 604/263 |
| 3,779,507 A | * | 12/1973 | Clarke | A61M 39/284 251/4 |
| 3,890,969 A | * | 6/1975 | Fischel | A61M 1/3624 128/DIG. 3 |
| 4,846,005 A | * | 7/1989 | Bacehowski | A61J 1/10 600/584 |
| 4,984,462 A | * | 1/1991 | Hass, Jr. | A61M 5/14 250/577 |
| 6,558,346 B1 | * | 5/2003 | Yoshioka | A61M 5/14244 604/118 |
| 2004/0064097 A1 | | 4/2004 | Peterson | |
| 2004/0177697 A1 | * | 9/2004 | Tokuhara | G01L 19/0654 73/715 |
| 2007/0135778 A1 | | 6/2007 | Murray et al. | |

(Continued)

*Primary Examiner* — Robert R Raevis
(74) *Attorney, Agent, or Firm* — The Webb Law Firm (57) ABSTRACT

A fluid container, such as an intravenous (IV) bag, including a fluid sensor for analyzing, identifying, and verifying a fluid is provided. The container includes an at least partially enclosed body defining an interior volume and one or more ports having an opening for accessing a fluid in the interior. A sensor device may be attachable to one of the ports. The sensor device includes a sensor for measuring a parameter of the fluid. A channel may extend between the port and the sensor for providing fluid from the interior volume of the body to the sensor. The sensor may be connected to a processing apparatus, such as a computer, for determining at least the type of fluid present based on the measured parameter obtained with the sensor. A method for analyzing, identifying, and verifying a fluid contained in a fluid container, such as an IV bag, is also provided.

19 Claims, 4 Drawing Sheets

(56) References Cited

U.S. PATENT DOCUMENTS

2011/0009817 A1 1/2011 Bennett et al.
2011/0062703 A1 3/2011 Lopez et al.
2011/0077480 A1 3/2011 Bloom et al.
2011/0111794 A1 5/2011 Bochenko et al.
2012/0065617 A1 3/2012 Matsiev et al.
2012/0226446 A1 9/2012 Nelson et al.

* cited by examiner

FLUID CONTAINER WITH FLUID IDENTIFICATION SENSOR AND METHOD

BACKGROUND OF THE DISCLOSURE

Field of the Disclosure

The present disclosure is related to the medical field and, more particularly, to a fluid container, such as an intravenous (IV) bag, and a method of analyzing, identifying, and verifying, fluid contained in the container.

Description of Related Art

IV bags are used for intravenous infusion of fluids, such as medicinal or therapeutic agents, volume expanders, blood-based products, blood substitutes, nutrient solutions, and buffer solutions during treatment of a patient. Typically, the IV bag is connected to a catheter or a needle through flexible medical tubing. The catheter or needle is inserted into a patient's vein at a vascular access site.

An IV bag is often formed from a flexible clear or translucent material, such as medical-grade polyvinyl chloride (PVC). Other suitable polymer materials may also be used for certain applications. The interior of the IV bag is accessible through a port or opening extending through a portion of the bag. The port may be covered by a piercable plug, stopper, or septa, which is often formed from an elastomeric material. The port may include a connector structure for attaching medical tubing to the port. Alternatively, the port may be an appropriate size to permit medical tubing to fit over a portion of the port to form a secure friction engagement or connection therewith.

When performing a medical procedure, it is normal for the technician, nurse, physician, or other medical professional, which are collectively referred to hereinafter as users, to verify that the contents of the IV bag are correct for the procedure being performed. Most simply, a label may be affixed to the bag that lists information about the fluid contained therein. For example, the label may include printed text with the name and concentration of the drug contained in the bag. The label may also include icons or pictures conveying additional information, such as warnings that the drug is contraindicated for certain patients. The label may also include various indicia that can be read by a scanner or imaging device, such as bar codes, QV codes, near field communications or radio frequency chips, and the like. The user is typically responsible for checking the label and, if necessary, scanning any readable indicia prior to performing any procedure.

A user may also test the solution of the IV bag directly to verify that the solution is correct for the procedure being performed. Optionally, this test may be performed by inserting a syringe into the interior of the bag through the port and drawing a small amount of fluid from the bag into the syringe. The extracted solution is expelled from the syringe to a test device, such as a test strip or lateral flow assay. The test strip or assay includes a reagent that reacts with the solution, indicating the type of solution provided. The fluid may also be provided to various electronic testing devices, meters, or sensors to identify the fluid solution.

In some medical applications, a solution is prepared immediately prior to delivery to a patient. In that case, the user obtains an IV bag filled with a first solution. The user inserts the syringe, as described above, and draws a predetermined amount of the first solution from the bag to create vacant space in the bag. The user then removes the syringe and inserts a new syringe, containing a second solution, such as a therapeutic agent, and injects the second solution into the bag to fill at least a portion of the vacant space. The bag can then be mixed by shaking or inverting the bag to ensure that the solutions are properly mixed together. The user may then test the mixed solution to verify that the desired concentration of solutions has been obtained.

However, testing fluid contents of an IV bag by drawing fluid from the bag and expelling the fluid to a testing device may be time consuming and inefficient. In addition, some therapeutic agents, such as chemotherapy agents, become toxic when mixed. Accordingly, it is often desirable to prevent the user from contacting the solution before or after mixing. Therefore, there is a need for a testing device or apparatus that is integrated with the bag or fluid infusion system to improve efficiency of the fluid testing and verification process. The testing apparatus should assist in identification of the fluid contents of the IV bag. The testing mechanism should also reduce or eliminate contamination opportunities, where the user comes into contact with any sort of toxic substance.

A number of electronic sensors and testing systems that are associated with an IV bag or infusion set are known. U.S. Pat. No. 5,563,584 to Rader et al. discloses a liquid level sensing system for a fluid infusion system. The sensing system includes a pressure sensor, such as a flexible diaphragm arrangement, connected to a port of an infusion bag. Various resistive or capacitive sensors may be used in place of a pressure sensor. Fluid flow through the port may be controlled by a valve. The pressure sensor is used to determine the volume of fluid in the IV bag and, if fluid volume is determined to be below a predetermined amount, to signal an alarm so that the IV bag can be refilled or replaced.

U.S. Pat. No. 8,066,127 to Coelho et al. discloses an apparatus and method for automatically separating whole blood contained in a fluid bag into separate components. Fluid flow from the bag is controlled by a valve. The valve is selectively opened and closed based on readings from a sensor that differentiates between the different blood components. The sensor may read various characteristics of the blood to differentiate between blood components, such as infrared emission, density, weight, radioactive emission, fluorescence, color, magnetism, or capacitance. The valve opens to allow fluid having a similar measured characteristic to be collected in a container. When a change in the measured characteristic is detected, the valve automatically closes to allow collection of the fluid in another container.

U.S. Pat. No. 8,425,487 to Beiriger et al. discloses a fluid delivery system including a vial spike for accessing the fluid contents of a medical vial. A sensor may be associated with the spike or with a fluid line extending from the vial. The sensor is used to confirm that the vial is correctly attached to the vial spike and that fluid is capable of flowing from the vial through the spike. The sensor may be an optical sensor, load sensor that detects the mass of the vial, or a conductivity sensor. The fluid delivery system may also include a frame having multiple needle spikes so that a number of vials can be simultaneously connected to the fluid delivery system.

Although the above-described systems provide some information about fluid volume in a container or about whether a good connection with the container is established, the known systems generally do not identify the type of fluid contained in the container.

SUMMARY OF THE DISCLOSURE

In view of the foregoing, there is a need for a testing device or apparatus that may be integrated with the bag or fluid infusion system to improve efficiency of the fluid testing and verification process. The testing apparatus should assist at least in identification of the fluid contents of the IV bag. The testing mechanism should also reduce or eliminate contamination opportunities, where the user comes into contact with any sort of toxic substance. Further, there is a need to develop improved fluid identification systems to improve safety and accuracy of drug delivery to patients. It is desirable that the system is easy for an operator to use and provides a fast and accurate indication of the substance contained in the fluid container or bag. The system should also effectively prevent the user or operator from coming into contact with the solution or substance during testing. The fluid container and method of identifying, verifying, and/or analyzing a fluid described herein in detail address these issues.

The present disclosure generally relates to a fluid container, such as an IV bag, that includes a fluid sensor for analyzing, identifying, and verifying a solution, as well as to methods for identification, verification, and analysis of a fluid. According to one potential embodiment, a fluid container for holding a fluid to be identified is provided. The container includes an at least partially enclosed body defining an interior volume, one or more ports having an opening for accessing a fluid in the interior, and a sensor device attached to one of the ports. The sensor device includes a sensor for measuring a parameter of the fluid to identify, verify, and/or analyze the fluid. The sensor device further includes a channel extending between the port and the sensor for providing fluid from the interior volume of the body to the sensor. The sensor may be connected to a processing apparatus, such as a computer, for determining at least the type of fluid present based on the measured parameter obtained with the sensor.

The at least partially enclosed body may comprise an intravenous bag made, for example, from a flexible material. The one or more ports may be a piercable septa extending over the opening. A hanger may be provided for attaching the container to a pole, stand, or support. The parameter to be measured by the sensor may be one of density, mass, volume, absorbance, transmittance, or any combination thereof. The sensor may comprise a sensing chip adapted to contact the fluid to be identified and embedded on a carrier substrate.

The sensor device may further comprise a sample well attached to the channel at an inflow port and defining an interior for holding fluid to be identified. The sample well may comprise an open top, and the sensor may comprise a mounting structure for removeably connecting the sensor to the open top, such that a portion of the sensor that contacts the fluid to be identified extends from the open top into the interior of the sample well. The sample well may comprise a fluid level line disposed on a sidewall of the well, the fluid level line indicating a volume of fluid required by the sensor. The sensor may be molded into a sidewall of the sample well.

The sensor device may further comprise a valve extending from a proximal end of the channel, the valve being transitionable from an open position in which fluid flow from the interior volume of the body to the sensor is permitted and a closed position in which fluid flow is prevented. The valve may be a one-way valve configured to permit fluid flow from the interior volume of the body to the sensor through the channel. The valve may close automatically after a predetermined volume of fluid passes through the valve. The valve may further comprise an annular cover configured to fit over a portion of one of the ports to removably attach the valve to the port. The sensor device may be integrally formed with one of the ports. The one or more ports on the body may comprise a fluid port configured to be connected to medical tubing for fluid delivery to a patient and a sensor port connected to the sensor device.

According to another aspect of the disclosure, an intravenous bag for containing a fluid is provided. The intravenous bag may include a body formed from a flexible material and defining an interior volume and a fluid port extending from the body for receiving expelling fluid from the interior volume of the body through the port. A sensor is provided on the body to measure a parameter of the fluid to, for example, identify the fluid contained therein. The sensor may comprise a sensing chip embedded to a carrier substrate, and the chip is in fluid communication with the interior volume of the body. The at least one parameter measured by the sensor may be one of density, mass, volume, absorbance, transmittance, or any combination thereof. The sensor may comprise a wired connector for connection to a processing apparatus.

In another aspect, a method of associating a fluid sensor to a fluid container is provided. The method includes providing a fluid container containing a fluid. The fluid container comprises an at least partially enclosed body defining an interior volume and one or more ports having an opening for accessing a fluid in the interior volume. The method further comprises providing a sensor device, the sensor device enclosing a sensor to measure at least one parameter of the fluid. Further, the method includes providing for fluid communication between the sensor and the interior volume of the body by connecting a channel between the port and the sensor for providing fluid from the interior volume of the body to the sensor. The method may further comprise expelling fluid from the interior volume through the channel to the sensor. The method may also further comprise measuring the at least one parameter of the fluid with the sensor, and identifying the fluid based, at least in part, on the measured parameter. The at least one parameter of the fluid measured by the sensor is density, mass, volume, absorbance, transmittance, capacitance, or any combination thereof.

Further details and advantages of the various embodiments described in detail herein will become clear upon reviewing the following detailed description of the various embodiments in conjunction with the accompanying drawing figures.

DESCRIPTION OF THE PREFERRED EMBODIMENTS

The illustrations generally show preferred and non-limiting embodiments of the systems and methods of the present disclosure. While the descriptions present various embodiments of the apparatus and system, it should not be interpreted in any way as limiting the disclosure. Furthermore, modifications, concepts, and applications of the disclosure's embodiments are to be interpreted by those skilled in the art as being encompassed, but not limited to, the illustrations and descriptions herein.

The following description is provided to enable those skilled in the art to make and use the described embodiments contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure. Further, for purposes of the description hereinafter, spatial orientation terms, if used, shall relate to the disclosure as it is oriented in the drawing figures. The term "proximal" refers to the direction toward the center or central region of the device. The term "distal" refers to the outward direction extending away from the central region of the device. However, it is to be understood that the disclosure may assume various alternative variations and step sequences, except where expressly specified to the contrary.

It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting. For the purpose of facilitating understanding of the disclosure, the accompanying drawings and description illustrate preferred embodiments thereof, from which the disclosure, various embodiments of its structures, construction and method of operation, and many advantages may be understood and appreciated.

With reference to the Figures, a fluid container, such as an IV bag 10, is illustrated. While the fluid container is referred to hereinafter as the IV bag 10, the fluid container may also be a medical vial, test tube, sample collection container, syringe barrel, cartridge, or other suitable container for holding a medical fluid or solution. The bag 10 includes a body that at least partially encloses an interior volume 12 (hereinafter "interior 12"). The volume of the interior 12 is chosen based on the particular medical procedure being performed, but is typically between about 250 mL and 1000 mL in the present embodiment. The bag 10 is configured to be connected to medical tubing (not shown) to allow fluid to flow from the interior 12 of the bag 10 through the tubing and to a patient. For example, the tubing may be connected to a catheter or needle inserted into a patient's vein at a vascular access site. The IV bag 10 is formed from a flexible translucent material, such as PVC. The bag 10 includes a hanger 14 for attachment to a stand or pole (not shown) to hold the bag 10 in an elevated position so that fluid can flow from the bag 10 to a patient by gravity. Other arrangements of an IV bag, medical tubing, and a catheter may also be used within the scope of the present disclosure. For example, fluid pumps, infusers, and the like may be connected to an infusion set and used to input into and draw fluid from the bag 10 and deliver fluid to a patient. Various sensors, testing apparatus, and the like may also be positioned along the medical tubing to determine fluid flow rate or other fluid delivery parameters. In addition, various access ports may be positioned along the medical tubing for permitting an operator or technician to inject additional fluid components into the fluid line or to draw fluid from the line.

The bag 10 includes one or more ports, referred to hereinafter, for convenience, as a fluid port 16 and a sensor port 18, extending from a bottom portion of the bag 10 and having an opening for accessing the interior 12 of the bag 10. The fluid port 16 is configured for connection with the medical tubing. The sensor port 18 is configured, in the present embodiment, to be connected to a sensor device 20 capable of analyzing, identifying and verifying fluid contents of the bag 10. The ports 16, 18 may be identical or the sensor port 18 may be specifically adapted for connection to the sensor device 20. The ports 16, 18 may be covered by a stopper or piercable septa 22. In certain embodiments, the ports 16, 18 include a connecting structure 24 such as a luer lock, press fit connection, or screw threads, for connecting medical tubing or other fluid conduits to the ports 16, 18. For example, the ports 16, 18 may be sized so that medical tubing or other fluid conduits fit over the connecting structure 24 to form a suitable friction engagement therewith. Various connectors, fasteners, or other attachment mechanisms may also be used for this purpose. In certain embodiments, the medical tubing may include a spike for accessing the interior 12 of the bag 10 through the piercable septa 22 and for establishing fluid communication between the bag 10 and tubing through the fluid port 16. Alternatively, the fluid port 16 may be covered or capped by a valve that can be opened to permit fluid flow therethrough.

Figure 1:
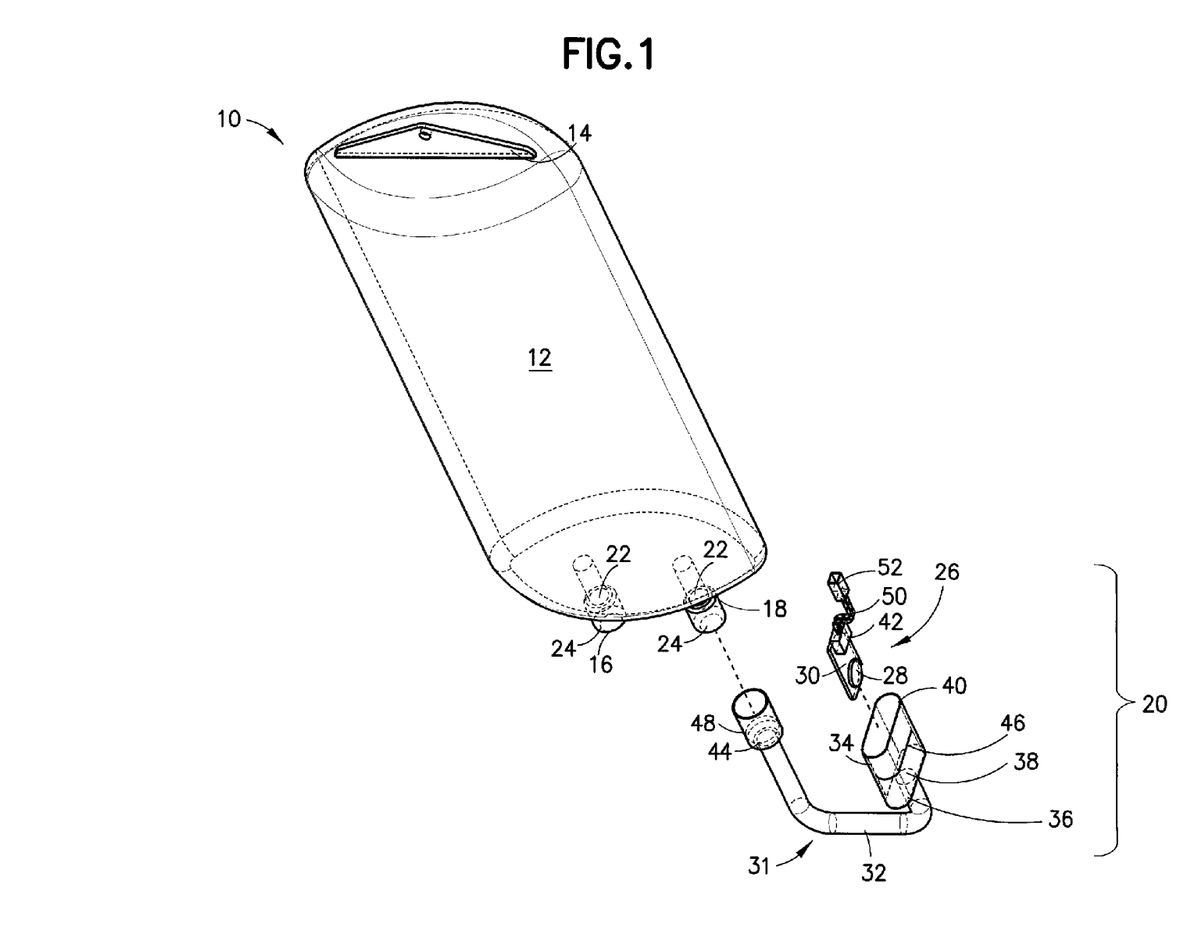
FIG. 1 is a schematic drawing of an expanded view of an embodiment of a fluid container, such as an IV bag, according to this disclosure.

With specific reference to FIG. 1, a non-limiting embodiment of an IV bag 10 is illustrated. The bag 10 includes a sensor device 20 connected to the sensor port 18 to permit fluid flow from the IV bag 10 to a sensor 26, which is positioned in the sensor device 20. The sensor 26 may be any type of sensor or meter capable of determining one or more parameters of a fluid. Desirably, the sensor 26 should be capable of measuring the parameter using only a small volume of the fluid, such as a few drops (such as less than 1 mL). In one embodiment, the sensor 26 is configured to measure fluid density. Based on measured density, the type of fluid or concentration of a medical or therapeutic agent can be calculated. In certain embodiments, the density sensor may be a pressure and volume sensor that calculates density based on the mass and volume of a fluid sample. The sensor 26 may also be an optical sensor that measures transmittance or absorbance of the solution to estimate density and composition. The sensor may also measure an electrical property of the fluid, such as capacitance.

In a non-limiting embodiment, the sensor 26 includes a sensing chip 28 embedded in a circuit board or other carrier substrate 30. The sensing chip 28 may be a silicon computer chip. The sensing chip 28 is configured to contact fluid to be tested and includes conductive circuitry that reacts with or produces a measurable electric signal when brought into contact with certain fluids. The chip 28 and/or substrate 30 may also include other micromechanical elements that oscillate or vibrate when exposed to certain types of fluid. The oscillation or vibration is sensed or recognized by the chip 28. A suitable micromechanical sensor array for measuring properties of fluids is disclosed in U.S. Patent Application No. 2012/0152001, to Reichel et al., incorporated herein by reference in its entirety. The sensor array includes a substrate having an opening. An oscillating plate-shaped element is positioned over the opening and permitted to oscillate when exposed to the fluid. A magnet disposed near the carrier substrate measures oscillation of the plate-shaped element. Oscillation of the plate is used to provide an indication of physical properties of the fluid being measured. Other known electrical sensors for measuring fluid properties may also be used within the scope of the present invention.

With continued reference to FIG. 1, the sensor device 20 includes a connector 31 or tubular member that defines a channel 32 extending between the sensor port 18 and a sample well 34. The sample well 34 is an oblong structure in the depicted embodiment having a substantially closed bottom portion 36 with an inflow port 38 connected to the channel 32. Fluid enters the well 34 through the inflow port 38 and collects in an interior of the well 34. The sample well 34 has an open top portion 40. The sensor 26 is removeably inserted into the sample well 34 through the open top portion 40. For example, the sensor 26 may include a mounting structure 42, such as a hook or fastener, that rests against or holds the sensor 26 to the top portion 40 of the well 34 during use.

The proximal end of the connector 31, which is connected to the sensor port 18, is covered by a valve 44, such as a manually operable one-way valve. The valve 44 may include a spike or other elongated member for accessing the interior 12 of the bag 10 through the septa 22 covering the port 18. The valve 44 is transitionable between an open position, in which fluid flow is permitted, to a closed position in which fluid flow is prevented. More specifically, when the valve 44 is actuated fluid flows from the interior 12 of the bag 10, through the port 18, and into the sample well 34. The valve 44 may close automatically after a predetermined amount of fluid passes through the valve 44. Alternatively, the valve 44 may be closed manually by the user. For example, the user may watch the fluid level in the sample well 34 rise a desired amount. To assist in determining when enough fluid is collected, the sample well 34 may include visual indicia, such as volume lines 46 that show the fluid volume and indicate when a sufficient amount of fluid has been collected. Once the desired fluid volume is drawn into the sample well 34, the user manually closes the valve 44.

With continued reference to FIG. 1, the valve 44 may include an annular or partially annular cover 48 or shroud. The cover 48 or shroud includes a connecting structure for attaching the sensor device 20 to the sensor port 18. For example, the annular cover 48 may define an interior diameter that is slightly larger than the outer diameter of the sensor port 18. Accordingly, the user can attach the cover 48 over the port 18 to create a frictional engagement that holds the sensor device 20 to the sensor port 18. Alternatively, various connectors or fasteners may also be used to hold the sensor device 20 in place.

The sensor 26 may be connected to a processing apparatus (not shown), such as a reader, scanner, controller, personal digital assistance (PDA), or computer via a wired connector 50. The sensor 26 may also be connected to such devices via a wireless connection. Optionally, the connector includes a plug 52 for insertion to the processing apparatus. Alternatively, the sensor 26 may be directly connected to the processing apparatus. The processing apparatus receives the measured parameter from the sensor 26. The value of the measured parameter may be compared with parameters for certain drugs and solutions stored on system memory, such as in a look up table. The processing apparatus may be configured to estimate the fluid type based on the closest values in the look up table. Alternatively, the processing apparatus may perform a calculation algorithm that compares multiple parameters or measured values to obtain a more accurate estimate of the fluid contents of the IV bag 10.

The measured parameter may also be used to determine the concentration of a drug or other therapeutic agent by performing a similar calculation. The estimated fluid type or concentration may be displayed to the user on a visual display connected to or associated with the processing apparatus. In more sophisticated systems, the processing apparatus may be integrated with a patient database including a patient's medical record. The stored medical record may include a list of procedures to be performed. If the identified fluid is not appropriate for a particular procedure, the processing apparatus may display an alert or warning to the user asking him or her to check the type of fluid being used. Similarly, the patient record may include information about a patient's allergies or other medications that the patient is taking. The processing apparatus may display a warning if a patient is allergic to a particular fluid or if the fluid is known to react unfavorably with other medications listed on the patient care record.

In use, a user provides an IV bag 10 filled with a solution to be administered to a patient. If the solution needs to be mixed with another solution or substances prior to delivery to the patient, the user inserts a syringe through one of the ports 16, 18 and injects the additional substance into the interior 12 of the IV bag 10. The user then mixes the bag 10 by shaking or inverting it. Once the solution is prepared, the user attaches the sensor device 20 to the sensor port 18 by pressing the valve 44 into the port 18, such that the cover 48 surrounds the port 18 to form a frictional engagement therewith. The user then assembles the sensor device 20 by inserting the sensor 26, including the chip 28, carrier substrate 30, and wired connector 50, into the sample well 34. The plug 52 extending from the wired connector 50 may be inserted into the processing apparatus and the processing apparatus may be turned on. The user then opens the valve 44, thereby allowing fluid to flow from the IV bag 10, through the channel 32 of the connector 31, and into the sample well 34. Fluid accumulates in the well 34 until it comes into contact with the chip 28 of the sensor 26. At this point, the valve 44 is closed manually or automatically. The sensor 26 measures a parameter of the fluid and transmits the measured value to the processing apparatus via the wired connector 50. Based on the measured parameter, the processing apparatus identifies the type of solution and/or the concentration of therapeutic agent in the fluid. Once the fluid contents of the IV bag 10 are identified and verified, the user may remove the sensor device 20 from the sensor port 18 by pulling the sensor device 20 away from the port 18. Alternatively, the sensor device 20 may remain connected to the sensor port 18 to perform additional fluid analysis at a later time. Once the fluid contents of the bag 10 are identified and verified, the user attaches the medical tubing to the fluid port 16 and prepares to deliver the fluid to the patient.

Figure 2:
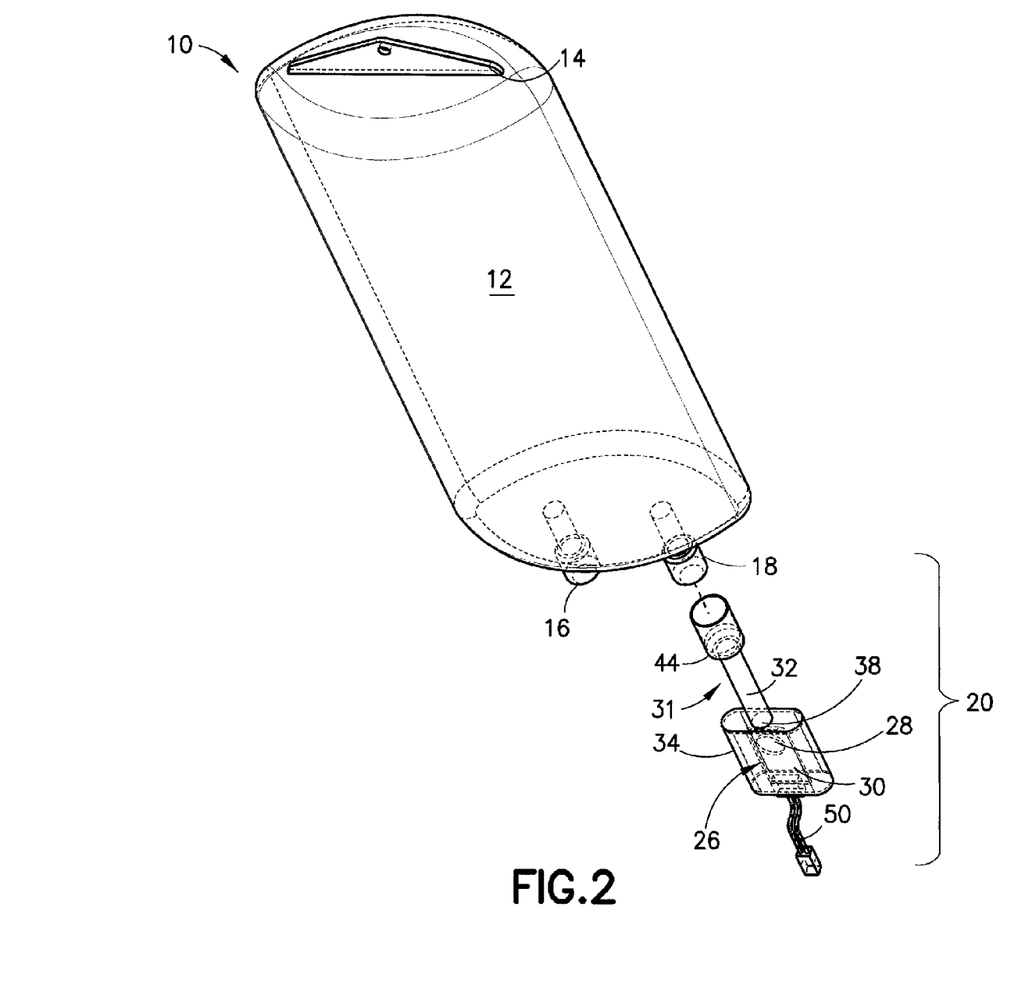
FIG. 2 is a schematic drawing of an expanded view of another embodiment of a fluid container, such as an IV bag, according to this disclosure.

With reference to FIG. 2, another embodiment of a fluid container, such as an IV bag 10, is illustrated. As in previously described embodiments, the IV bag 10 is formed from a flexible material and includes two ports, namely the fluid port 16 and the sensor port 18. The sensor device 20 and the sensor 26 are connected to the bag 10 through the sensor port 18. However, in contrast to the previously described embodiment, the sensor 20 cannot be removed from the sample well 34. Instead, the sample well 34 is a substantially enclosed structure including an inflow port 38 at a top portion thereof. The sensor 26, including the chip 28 and carrier substrate 30, are molded to a sidewall of the well 34, such that the sensing chip 28 comes into contact with fluid contained in the well 34. The wired connector 50 extends from the sample well 34, and can be connected to the processing apparatus. As in previously described embodiments, the sensor device 20 includes a valve 44 connected to the well 34 through the channel 32 of the connector 31. The valve 44 is configured to be inserted in the sensor port 18. The sensor device 20, including the valve 44, sample well 34, connector 31, and sensor 26, can be removed from the sensor port 18 by pulling the sensor device 20 in a distal direction away from the port 18.

Figure 3:
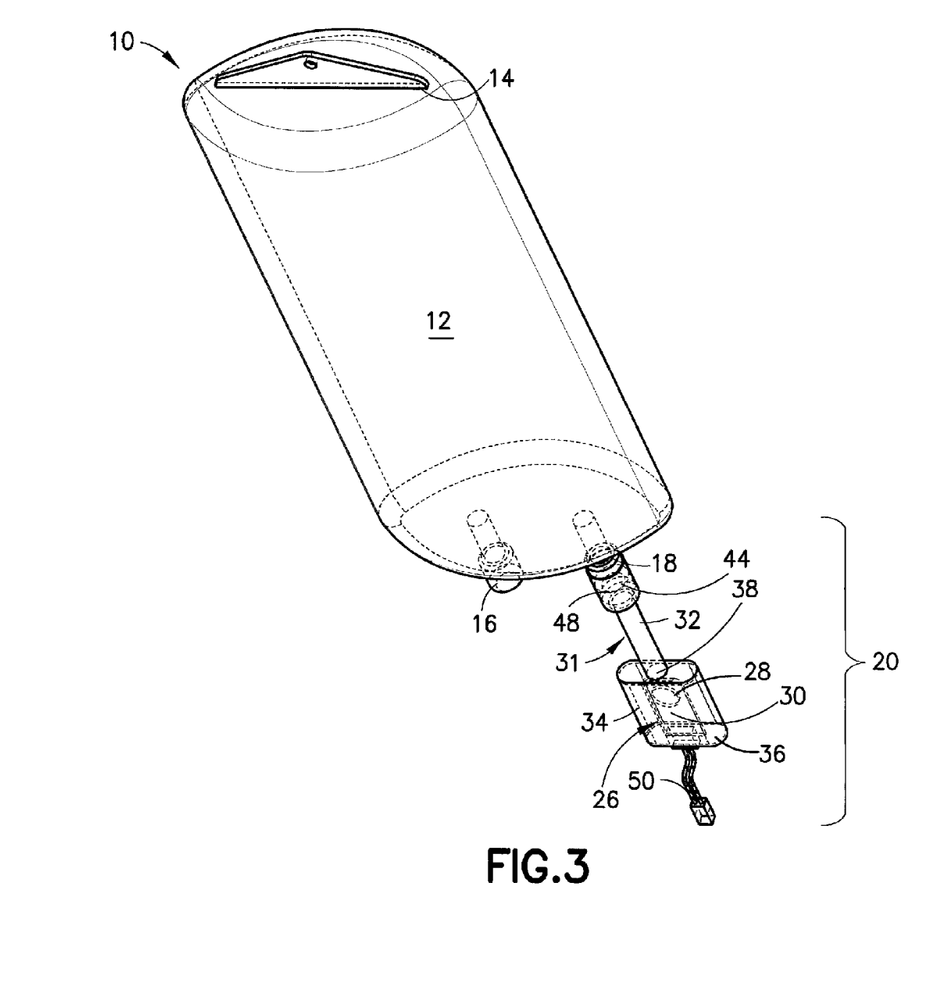
FIG. 3 is a schematic drawing of further embodiment of a fluid container, such as an IV bag, according to this disclosure.

With reference to FIG. 3, another embodiment of a fluid container, such as an IV bag 10, is illustrated. As in previously described embodiments, the bag 10 includes two ports, namely the fluid port 16 and the sensor port 18. The sensor port 18 is connected to the sensor device 20. Unlike in previously described embodiments, the sensor device 20 is integrally formed with or permanently connected to the bag 10 through the sensor port 18. More specifically, the proximal end of the sensor device 20 including the valve 44 is non-removeably inserted to the sensor port 18. For example, an interior surface of the cover 48 extending around the valve 44 may include an adhesive for attaching the cover 48 to the sensor port 18. Alternatively, the port 18 may include a connecting structure, such as a ridge or detent, which maintains the connection between the sensor device 20 and port 18. As in previously-described embodiments, the valve 44 is connected to the sample well 34 through the channel 32 of the connector 31. The sample well 34 is a substantially enclosed structure accessible through the inflow port 38 that connects the connector 31 to the sample well 34. The sensing chip 28 and carrier substrate 30 are integrally formed with a sidewall of the sample well 34, such that fluid contained in the well 34 contacts the chip 28 to measure fluid parameters thereof. The wired connected 50 extends from a bottom portion 36 of the well and can be connected to the processing apparatus.

Figure 4:
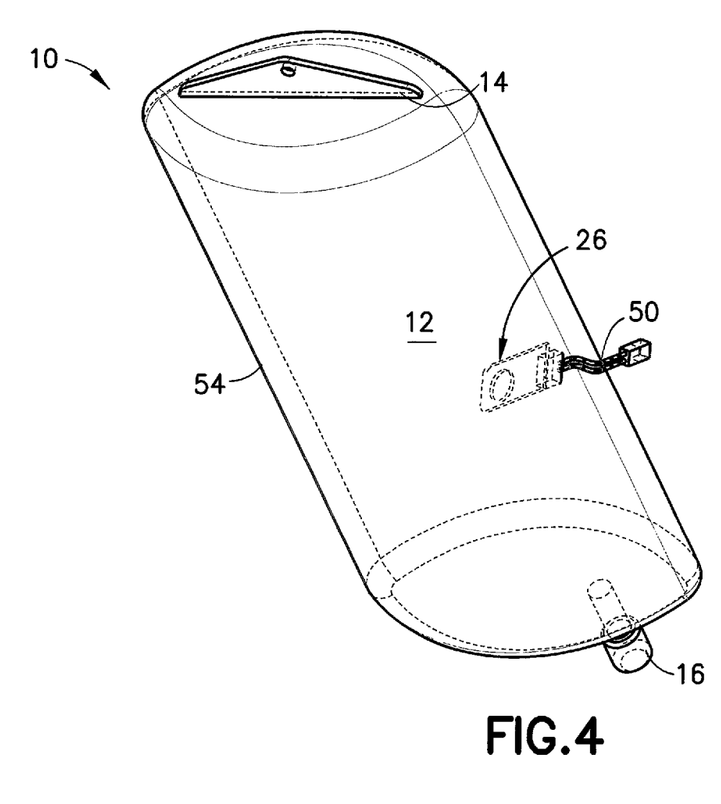
FIG. 4 is a schematic drawing of yet another embodiment of a fluid container, such as an IV bag, according to this disclosure.

With reference to FIG. 4, another embodiment of a fluid container, such as an IV bag 10, is illustrated. As in previously-described embodiments, the IV bag 10 includes the fluid port 16, which is configured to be connected to medical tubing for fluid delivery to a patient. The IV bag 10 includes a body portion 54 formed from a flexible material and defining the interior volume 12. The bag 10 includes the sensor device 20 for measuring a parameter of the fluid. The sensor device 20 is integrally formed with a sidewall of the body portion 54 of the bag 10. For example, the sensor device 20 may be molded within the body 54 of the bag 10 during manufacture, such that at least a portion of the sensor device 20 is able to access fluid positioned in the interior 12 of the bag 10. The sensor device 20 includes the wired connector 50 for connecting the sensor device 20 to the processing apparatus. Alternatively, a wireless connection may be provided between the sensor device 20 and the processing apparatus. As in previously described embodiments, the measured parameter obtained by the sensor 20 is used to identify and verify the fluid contents of the bag prior to fluid delivery to a patient.

While embodiments of the IV bag 10 and method of fluid identification were provided in the foregoing description, those skilled in the art may make modifications and alterations to these embodiments without departing from the scope and spirit of the disclosure. Accordingly, the foregoing description is intended to be illustrative rather than restrictive. The disclosure described hereinabove is defined by the appended claims and all changes to the disclosure that fall within the meaning and the range of equivalency of the claims are to be embraced within their scope.

The invention claimed is:

1. A container for holding a fluid to be identified, the container comprising:
an at least partially enclosed body defining an interior volume;
at least one fluid port having an opening for accessing the interior volume and configured to be connected to medical tubing for fluid delivery from the interior volume to a patient;
at least one sensor port having an opening for accessing the fluid in the interior volume; and
a sensor device attached to the at least one sensor port, the sensor device comprising a sensor for measuring density of the fluid and a connector enclosing a channel extending between the sensor port and the sensor for providing fluid from the interior volume of the body to the sensor.

2. The container of claim 1, wherein the at least partially enclosed body comprises an intravenous bag.

3. The container of claim 1, wherein the fluid port and/or the sensor port include a piercable septa extending over the opening.

4. The container of claim 1, further comprising a hanger for attaching the container to a pole, stand, or support.

5. The container of claim 1, wherein the sensor comprises a sensing chip adapted to contact the fluid to be identified and embedded on a carrier substrate.

6. The container of claim 1, wherein the sensor device further comprises a sample well attached to the connector at an inflow port and defining an interior for holding the fluid to be identified.

7. The container of claim 6, wherein the sample well comprises an open top, and wherein the sensor device further comprises a mounting structure for removeably connecting the sensor to the open top of the sample well, such that a portion of the sensor that contacts the fluid to be identified extends from the open top into the interior of the sample well.

8. The container of claim 6, wherein the sample well comprises a fluid level line disposed on a sidewall of the well, the fluid level line indicating a volume of fluid required by the sensor.

9. The container of claim 6, wherein the sensor is molded into a sidewall of the sample well.

10. The container of claim 1, wherein the sensor device further comprises a valve extending from a proximal end of the channel, the valve being transitionable from an open position in which fluid flow from the interior volume of the body to the sensor is permitted and a closed position in which fluid flow is prevented.

11. The container of claim 10, wherein the valve is a one-way valve configured to permit fluid flow from the interior volume of the body to the sensor through the channel.

12. The container of claim 1, wherein the sensor device is non-removeably attached to the sensor port.

13. A container for holding a fluid to be identified, the container comprising:
an at least partially enclosed body defining an interior volume;
at least one fluid port having an opening for accessing the interior volume and configured to be connected to medical tubing for fluid delivery from the interior volume to a patient;
at least one sensor port having an opening for accessing the fluid in the interior volume; and
a sensor device attached to the at least one sensor port, the sensor device comprising:
a sensor for measuring at least one parameter of the fluid;

a connector enclosing a channel extending between the sensor port and the sensor for providing fluid from the interior volume of the body to the sensor; and a valve extending from a proximal end of the channel, the valve being transitionable from an open position in which fluid flow from the interior volume of the body to the sensor is permitted and a closed position in which fluid flow is prevented, wherein the valve closes automatically after a predetermined volume of fluid passes through the valve.

14. The container of claim 13, wherein the at least one parameter measured by the sensor is one or more of density, mass, and volume.

15. A container for holding a fluid to be identified, the container comprising:
   an at least partially enclosed body defining an interior volume;
   at least one fluid port having an opening for accessing the interior volume and configured to be connected to medical tubing for fluid delivery from the interior volume to a patient;
   at least one sensor port having an opening for accessing the fluid in the interior volume; and
   a sensor device attached to the at least one sensor port, the sensor device comprising:
      a sensor for measuring at least one parameter of the fluid;
      a connector enclosing a channel extending between the sensor port and the sensor for providing fluid from the interior volume of the body to the sensor;
      a valve extending from a proximal end of the channel, the valve being transitionable from an open position in which fluid flow from the interior volume of the body to the sensor is permitted and a closed position in which fluid flow is prevented; and
      an annular cover configured to be attached over a portion of the sensor port to removeably attach the valve to the sensor port.

16. The container of claim 15, wherein the at least one parameter of the fluid measured by the sensor is one or more of density, mass, and volume.

17. A method of associating a fluid sensor to a fluid container comprising:
   providing the fluid container containing a fluid, the fluid container comprising:
      an at least partially enclosed body defining an interior volume;
      at least one fluid port having an opening for accessing the interior volume and configured to be connected to medical tubing for fluid delivery from the interior volume to a patient; and
      at least one sensor port having an opening for accessing the fluid in the interior volume;
   providing a sensor device, the sensor device enclosing a sensor configured to measure density of the fluid; and
   attaching the sensor device to the sensor port, thereby providing for fluid communication between the sensor and the interior volume of the body through a channel between the sensor port and the sensor for providing fluid from the interior volume of the body to the sensor.

18. The method of claim 17, further comprising expelling fluid from the interior volume through the channel to the sensor.

19. The method of claim 18, further comprising:
   measuring the density of the fluid with the sensor; and
   identifying the fluid based, at least in part, on the measured density.

* * * * *